United States Patent [19]

Dissing et al.

[11] Patent Number: 5,370,124
[45] Date of Patent: Dec. 6, 1994

[54] CARDIAC ASSIST DEVICE AND METHOD, INCLUDING DETECTION OF HEART EVENTS

[75] Inventors: Bo Dissing, Kista; Agneta Elmhammer, Stockholm, both of Sweden

[73] Assignee: Siemens Aktiengesellschaft, Munich, Germany

[21] Appl. No.: 84,586

[22] Filed: Jul. 1, 1993

[30] Foreign Application Priority Data

Jul. 31, 1992 [EP] European Pat. Off. ........ 92113111.6

[51] Int. Cl.$^5$ ............................................. A61N 1/00
[52] U.S. Cl. ..................................... 128/696; 607/28
[58] Field of Search ............................ 128/695–697, 128/700, 704, 901; 607/5, 6, 9, 28

[56] References Cited

U.S. PATENT DOCUMENTS

| | | |
|---|---|---|
| 4,708,144 | 11/1987 | Hamilton et al. . |
| 4,768,511 | 9/1988 | DeCote, Jr. . |
| 4,827,934 | 5/1989 | Ekwall . |
| 4,960,123 | 10/1990 | Maker ........................ 128/901 |
| 5,010,887 | 4/1991 | Thornander ................. 128/696 |
| 5,025,794 | 6/1991 | Albert et al. ................ 128/696 |

FOREIGN PATENT DOCUMENTS 0321764 6/1989 European Pat. Off. .
0350160 1/1990 European Pat. Off. .

*Primary Examiner*—Lee S. Cohen
*Assistant Examiner*—Marianne H. Parker
*Attorney, Agent, or Firm*—Hill, Steadman & Simpson

[57] ABSTRACT

Heart events are identified within an electrical signal derived from the heart by determining when the signals exceed a threshold which is matched to the signal height of the electrical signal dependent on a chronological average value of the detection margins of the signal that exceed the threshold in successive detection events. In order to suppress the influence of noise-like disturbing signals that appear in isolation on the control of the threshold but to nonetheless achieve an adequately fast adaptation of the threshold to rapid, substantial changes of the electrical signal despite the formation of an average value, the formation of the average value ensues over a time interval corresponding to the duration of only a few breaths and a change of the threshold ensues only when the average value respectively upwardly or downwardly transgresses upper or lower the limit values of a switching hysteresis.

14 Claims, 2 Drawing Sheets

CARDIAC ASSIST DEVICE AND METHOD, INCLUDING DETECTION OF HEART EVENTS

BACKGROUND OF THE INVENTION

1. Field of the Invention

The present invention relates to a cardiac assist device and method, including an apparatus and method for detecting heart events such as for use in controlling the stimulation of a heart with a cardiac pacemaker.

2. Description of the Prior Art

An apparatus for detecting heart events is disclosed in U.S. Pat. No. 4,708,144 which includes a signal pick-up for acquiring an electrical signal dependent on the heart events, and a threshold detector following the signal pick-up for generating a detection signal indicating the presence of a heart event when the electrical signal exceeds a prescribed threshold. A signal evaluation means identifies the current signal height of the electrical signal exceeding the threshold with reference to the threshold. An averaging unit forms an average value from the threshold-related signal heights identified during a prescribed time interval. A control unit sets the threshold in relationship to the acquired, electrical signal dependent on the average value that has been formed, whereby the threshold is raised in relationship to the electrical signal given an increasing average value and is lowered given a decreasing average value.

The apparatus disclosed in U.S. Pat. No. 4,708,144 is a component of an implantable heart pacemaker and serves the purpose of detecting spontaneous heart events via the electrical signal of the intracardial electrogram, and thus controls the heart pacemaker. Given, for example, a single chamber heart pacemaker, it is thus possible to inhibit the stimulation of the heart given the appearance of detected, natural heart beats or—given a double chamber heart pacemaker—to synchronize the stimulation of one chamber with the heart events detected in the other chamber. A reliable detection of heart events requires a detection sensitivity that, on the one hand, is adequately high in order to be able to identify the signal component dependent on the heart activities from the acquired electrical signal, but is not so high that disturbances and noise signals (background components) are erroneously detected as heart events. Further, the selection of a defined detection sensitivity is made more difficult because the acquired electrical signal can change over a long term, for example because the electrodes employed for the derivation of the intracardial electrogram grow over after implantation over a longer time span in the heart.

An automatic matching of the detection sensitivity to the acquired electrical signal ensues in this known apparatus by using only heart events, among those which are detected, having an electrical signal which exceeds the aforementioned threshold; the threshold is set relative to the electrical signal by forming an average value from the signal heights of the electrical signals that exceed the threshold at every heart event during a time interval having a length in the range from at least a few minutes up to the order of magnitude of hours. The electrical signal is amplified with a variable gain dependent on the average value before it proceeds to the threshold detector. The threshold itself is set to an invariable value.

As disclosed in U.S. Pat. No. 4,827,934, however, it is also possible to modify the threshold itself for adapting the detection sensitivity to the electrical signal. Since the threshold is variable in this case, the detection margin, i.e. the respective spacing between the threshold and the signal height of the electrical signal exceeding the threshold, rather than the signal height itself, is utilized as parameter for setting the threshold. The conditions resulting in a variation of the threshold however, are not discussed in U.S. Pat. No. 4,827,934.

It is assumed in the adaptation of the detection sensitivity described in the aforementioned U.S. Pat. No. 4,708,144 that the signal parts of the acquired electrical signal which correlate with the heart events to be detected are exhibit only extremely slow change, for which reason the formation of the average value that is undertaken ensues over several minutes up to several hours. Although this known device is successful in nearly completely eliminating the influence of noise signals on the setting of the detection sensitivity, the adaptation of the detection sensitivity to, for example, a rapidly steady or a suddenly discontinuous variation of the electrical signal ensues corresponding slowly since such a change—due to the long time interval for averaging the signal height of the electrical signal—arises only relatively late in the average value that serves as the parameter for changing the detection sensitivity. Such sudden or rapid changes of the electrical signal can be based on suddenly occurring disturbing influences such as noise signals from the outside, changes in the electrode position, or sudden changes of the heart signals itself, for example after extra heartbeats or given an infarction, and can therefore cannot be precluded.

SUMMARY OF THE INVENTION

It is an object of the invention to provide an automatic adaptation of the detection sensitivity to the electrical signal taken from the heart in the detection of heart events, wherein changes of the electrical signal that are noise-like and occur in isolation do not influence the setting of the detection sensitivity whereas rapid, substantial changes in the electrical signal lead to an appropriate, rapid adaptation of the detection sensitivity.

The above object is achieved in a cardiac assist device and method, which include the detection of signals, in accordance with the principles of the present invention wherein the length of the time interval for forming the average value in an apparatus of the type disclosed in U.S. Pat. No. 4,708,144 corresponds to the average duration of a small number of breaths (such as a few breaths), and wherein a switching hysteresis is generated having a lower limit value and an upper limit value, whereby a re-setting of the threshold only ensues when the average value either falls below the lower limit value or exceeds the upper limit value.

Disturbances in the electrical signal that appear in isolation such as, for example, extra heartbeats, as well as respiration-caused variation of the electrical signal and noise signals are largely suppressed by the formation of the average value over the comparatively short time interval amounting to less than one minute. Influences on the average value proceeding beyond this due to such disturbances have no influence on the setting of the detection sensitivity in the apparatus of the invention because the changes in the average value that are caused only by disturbances within the switching hysteresis that is provided. Substantial changes of the electrical signal lead to the average value respectively upwardly or downwardly exceeding the upper and lower limit value of the switching hysteresis relatively quickly because of the short time interval for the formation of the average value, so that a rapid adaptation of the detection sensitivity to the variations in the electrical signal correspondingly ensues. The contradictory demands in the automatic setting of the detection sensitivity are thus met in this manner, namely to suppress the influence of disturbing signals to the farthest-reaching extent by formation of an average value while still achieving an appropriate, fast adaptation of the detection sensitivity given a rapid, substantial variation of the acquired electrical signal. Moreover, the device of the invention has the advantage that the calculating outlay required for the formation of the average value is correspondingly low because of the short time intervals for the averaging.

As already discussed in conjunction with the initially cited prior art, the setting of the threshold in relationship to the acquired electrical signal, i.e., the change in the detection sensitivity, can ensue either by amplifying the electrical signal supplied to the threshold detector with a variable gain given a permanently prescribed threshold, or by varying the threshold itself. In the former instance, the signal heights of the electrical signal respectively identified at the detected heart events can be directly utilized for the formation of the average value, whereas the detection margins, i.e. the spacing between the identified signal heights and the respectively current threshold, are subject to the formation of the average value in the latter instance. At every readjustment of the threshold, the values for the signal heights utilized for the formation of the average value with reference to the threshold change correspondingly. In order to prevent the signal heights that were identified before the change in the threshold that caused the resetting of the threshold, and which were thus determined with reference to the preceding threshold, from entering into the new average value formation, it is provided in accordance with the invention that all signal heights utilized for the formation of the average value are determined with reference to the new threshold after every resetting of the threshold. This can occur by normalizing in that the signal heights that were identified before the variation of the threshold, and which enter into the new average value formation, with the new threshold, or by using only the signal heights that are identified after the resetting of the threshold for the formation of the average value after every resetting of the threshold.

In an embodiment of the method and device of the invention, the length of the time interval is prescribed by a predetermined plurality preferably 10 through 30, of successively detected heart events. For example, the signal heights of the eighteen most recently detected heart events can be utilized for the formation of the average value, which corresponds to a formation of the average value over the duration of a few breaths. As used herein, "a few breaths" means approximately three average breaths, i.e., approximately three breaths arising when the subject is in a stable, non-exertive mode. The predetermination of the plurality of heart events utilized for the formation of the average value makes it possible to provide a average value memory having a corresponding, limited plurality of memory locations for the formation of the average value, whereby the value of the signal height of the electrical signal identified at every detected heart event replaces the oldest stored value in the memory.

The device of the invention can be a demand heart pacemaker, and the method can be practiced in a demand pacemaker wherein the output of a stimulation pulse ensues when a spontaneous heart event is not detected by the apparatus of the invention within a base time interval that follows a preceding stimulation or detection of a spontaneous heart event. In order to be able to reliably detect the appearance of a natural heart event after a stimulation pulse or a sequence of stimulation pulses, in accordance with the invention the threshold of the threshold detector is lowered in relationship to the electrical signal by a prescribed amount after a first output of a stimulation pulse following a detection of a spontaneous heart event.

It cannot be precluded both in the known device as well as in the apparatus and method of the invention for detecting heart events that disturbing signals exceed the currently-set threshold and are thus erroneously detected as heart events. An example of this is that the T-wave may also exceed the threshold in an intracardial electrogram in addition to the QRS complex, so that a respective heart event is detected in both instances. In order to reduce the risk of such misdetections, it is provided in a further embodiment of the method and device of the invention that the beat-to-beat variance of the signal heights is identified and utilized for the formation of the average value, and the threshold of the detector is raised by a given amount when the variance exceeds a given value. Normally the signal height of successive, normal heart events varies only slightly, so that a higher variance is to be attributed to the detection of signals that differ in comparison to the "target" heart events.

Since the risk of misdetections becomes greater as the detection sensitivity is set higher, or the threshold is set lower, and in order to prevent the threshold from becoming "pegged" at the low level due to misdetections, the identification of the variance is preferably triggered when the current threshold of the threshold detector is set below a minimum value.

DESCRIPTION OF THE PREFERRED EMBODIMENTS

Figure 1:
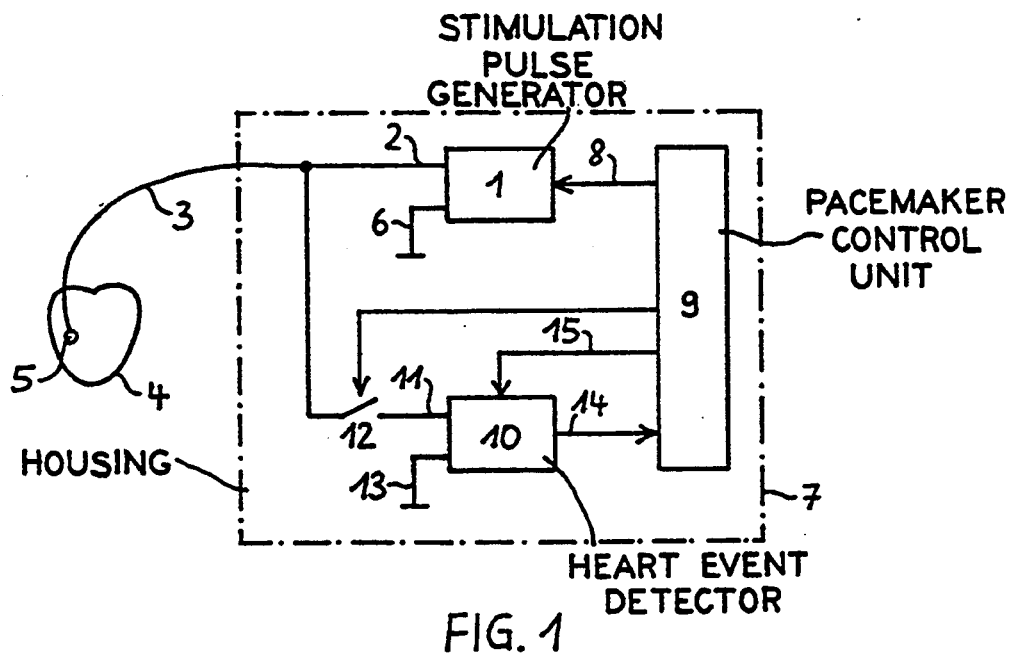
FIG. 1 is a schematic block diagram of an example of a heart pacemaker containing the apparatus of the invention and operating in accordance with the method of the invention.

FIG. 1 shows a block circuit diagram of a heart pacemaker including a stimulation pulse generator I having a first output terminal 2 connected via an electrode line 3 to a stimulation electrode 5 arranged in the heart 4. The second output terminal 6 of the stimulation pulse generator 1 is connected to a housing 7 of the heart pacemaker that serves as the return electrode for the stimulation electrode 5. The stimulation pulse generator 1 is connected via a control line 8 to a heart pacemaker control 9 that initiates the output of stimulation pulses by the stimulation pulse generator 1 via the control line 8. A detector apparatus 10 for detecting spontaneous heart events, constructed and operating in accordance with the invention, has a first input terminal 11 connected to the electrode 5 via a switch 12 controllable by the heart pacemaker control unit 9 and has a second input terminal 13 connected to the housing 7 of the heart pacemaker. The detector apparatus 10 is connected to the heart pacemaker control unit 9 via an output 14, that indicates the detection of a heart event and is controlled by the heart pacemaker control unit 9 via a further control line 15.

A base time interval is started within the heart pacemaker control unit 9 after each output of a stimulation pulse by the stimulation pulse generator 1 or after the detection of a spontaneous heart event by the detector apparatus 10. After the expiration of a refractory time, the controllable switch 12 is simultaneously closed by the heart pacemaker control unit 9 in order to be able to detect the occurrence of a natural heart event with the detector apparatus 10. When such a heart event is detected before the expiration of the base time interval, the base time interval is restarted without a stimulation pulse being generated. When, by contrast, the base time interval expires without a natural heart event being detected, a stimulation pulse is output to the heart 4 and the base time interval is restarted.

Figure 2:
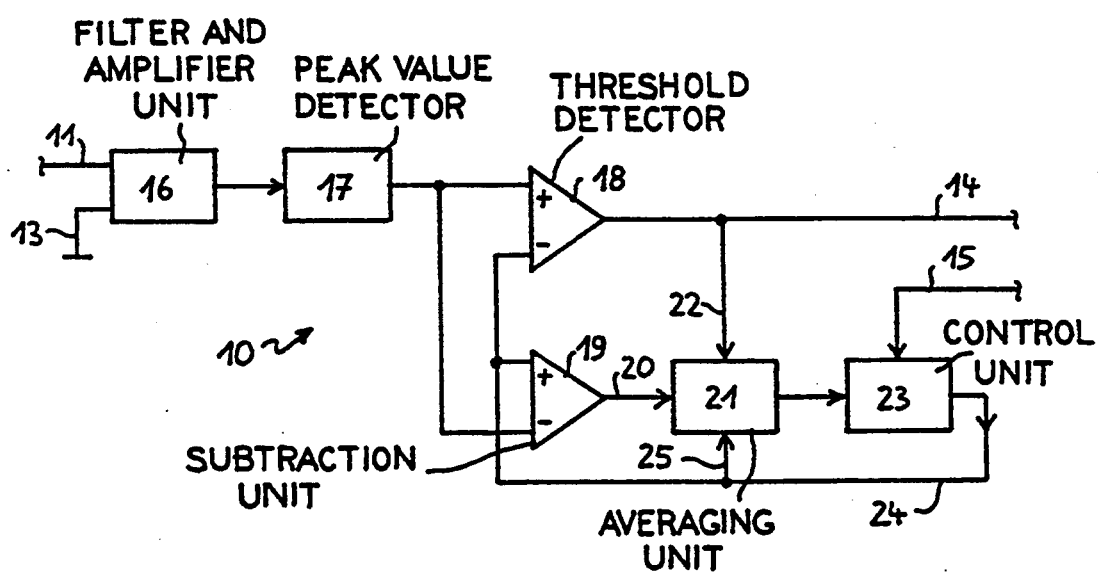
FIG. 2 is a schematic block circuit diagram of the apparatus of the invention.

FIG. 2 shows a block circuit diagram of an exemplary embodiment of the detector apparatus 10 for detecting heart events. The electrical signal of the intracardial electrogram acquired between the input terminals 11 and 13 is first supplied to a filter and amplifier unit 16, in which the frequency components characteristic for the heart events to be detected are filtered out of the electrical signal. Further, the signal is subjected to signal conditioning in which signal properties typical of the heart events to be detected, such as, for example, a prescribed minimum steepness of the signal edges or a specific signal width are converted into a variation of the signal height. This can be accomplished, for example, by differentiation or integration of the electrical signal. The electrical signal conditioned in this manner proceeds from the filter and amplifier unit 16 to a peak value detector 17 wherein the signal height of the electrical signal is identified. The value for the signal height is supplied to the non-inverting input (+) of a threshold detector 18 whose inverting input (−) is supplied with a variable threshold signal. When the value for the signal height upwardly transgresses the threshold, the threshold detector 16 generates an output signal via the output 14 of the detector apparatus 10 to the heart pacemaker control unit 9 that indicates the detection of a heart event.

For setting the threshold, the threshold signal together with the value for the signal height are supplied to both inputs of a subtraction unit 19 that generates a signal at its output 20 that corresponds to the detection margin, i.e., to the spacing between the threshold and the value of the signal height. The detection margin, which also represents a measure for the signal height with reference to the threshold, is supplied to an averaging unit 21 for forming an average value. The averaging unit 21 is connected via a first control input 22 to the output 14 of the threshold detector 18 (serving as the output of the detector device 10) which assumes the value of the detection margin at the output of the subtraction unit 19 only when the presence of a heart event had been detected by the threshold detector 18. An average value is formed in the averaging unit 21 from the newly read-in value of the detection margin and a prescribed plurality of most recently read-in values. The plurality of values utilized for the formation of the average value can, for example, amount to eighteen, which corresponds to an averaging over a duration of eighteen heart beats or approximately three breaths given a normal heart activity. Accordingly, the averaging unit 21 contains an average value memory (not shown) having a plurality of eighteen memory locations, whereby the value of the detection margin calculated at every detected heart event is read into the memory instead of the respectively oldest, stored value.

The average value generated in the averaging unit 21 is utilized in a following control unit 23 for setting the threshold supplied to the threshold detector 18 and to the subtraction unit 19 via an output 24 of the control unit 23. Each change of the threshold ensues with a switching hysteresis, by raising the threshold when the average value upwardly exceeds an upper limit value of the switching hysteresis and by lowering the threshold when the average value downwardly transgresses a lower limit value of the switching hysteresis. The amount of the change of the threshold is selected such that the new threshold has a given relationship to the detection margin. Given a selected relationship of 1:1, thus, the signal height is twice as high as the threshold. The output 24 of the control unit 23 is additionally connected to a reset input 25 of the averaging unit 21. After every change of the threshold, the values for the detection margin that were read into the averaging unit 21 for the change are reset via this reset input 25 in order to prevent the values for the detection margins based on a new threshold from being mixed with the values of the detection margins based on the old threshold in the following formation of the average value.

Further, a control function is implemented in the control unit 23, this control function, when the threshold is set below a minimum value, comprising a calculation algorithm for determining the beat-to-beat variance of the signal parts that are supplied to the averaging unit 21 and that upwardly transgress the threshold; when the variance of the average value thereby exceeds a prescribed value, the threshold is raised by a prescribed amount.

A further control function of the control unit 23 comprises lowering the threshold by a prescribed amount after a first output of a stimulation pulse that follows a detection of a spontaneous heart event, this output being reported to the control unit 23 via the control line 15.

Figure 3:
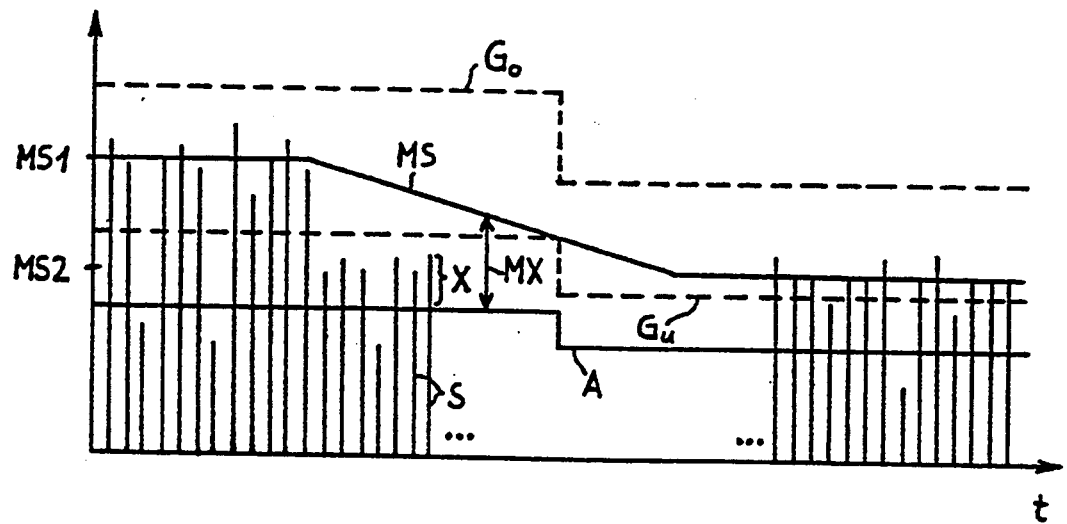
FIG. 3 is a diagram showing an example of the setting of the detection sensitivity of the apparatus shown in FIG. 2 in relationship to the electrical signal to be acquired.

In a diagram, FIG. 3 shows an example of the change of the threshold A dependent on the average value MX of the detection margin X between the electrical signal S and the threshold A. For a simpler illustration, the electrical signal S is shown in the form of discrete-time samples with different signal heights; the signal S, however, can also be a chronologically continuous signal. The average value of the electrical signal S, formed over a time interval of 20 successive samples, is referenced MS. As FIG. 3 shows, the signal heights of the electrical signal S initially fluctuate around a first average value MS1. A detection of a heart event is registered every time the signal height of the electrical signal S exceeds the prescribed threshold A. The part of the signal height exceeding the threshold A forms the detection margin X. The average value of the detection margins X over a predetermined plurality of past detection events is referenced MX. Signal values of the electrical signal S that do not exceed the threshold A do not contribute to the formation of the average value.

As long as the curve of the average value MX of the detection margins proceeds between the lower limit value $G_u$ and the upper limit value $G_o$ of a switching hysteresis, the threshold A is not varied. In the case of the examples shown in FIG. 3, the signal heights of the electrical signal S suddenly decrease and stabilize at a new value around MS2. The curve of the average value MX of the detection margins follows the change of the signal heights with a delay caused by the formation of the average value. Since the formation of the average value, however, ensues only over a relatively short time interval, the delay is correspondingly slight. As soon as the average value MX thereby falls below the lower limit value $G_u$, the threshold A is lowered by a defined amount, so that the average value MX of the detection margins is again set to a ratio of 1:1 with respect to the new threshold A. The limit values $G_u$ and $G_o$ of the switching hysteresis are also varied with the variation of the threshold A, but the relationship of the limit values $G_u$ and $G_o$ to the threshold A remains unvaried. For that case not shown in FIG. 3 wherein the curve of the average value MX of the detection margins exceeds the upper limit value $G_0$, the threshold A is raised by a given amount, so that an adequately high main detection margin MX is again achieved.

Figure 4:
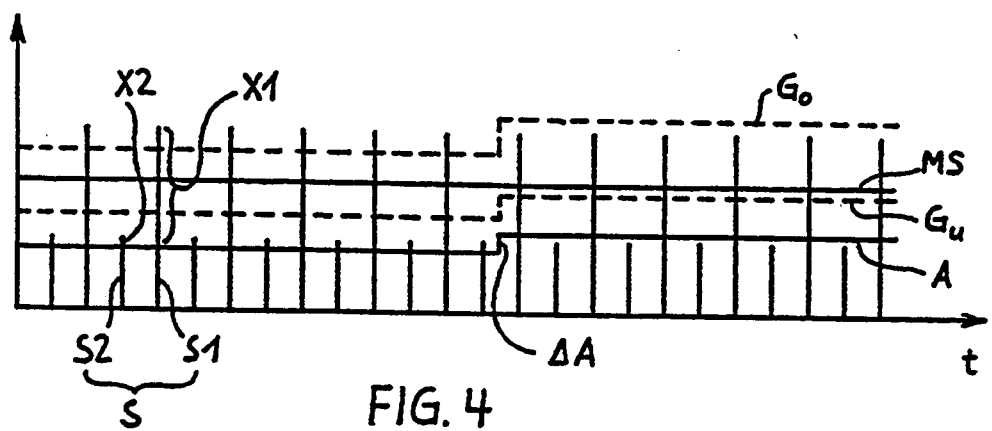
FIG. 4 shows an example of the variation of the detection sensitivity given a high variance of the detection margin in accordance with the invention.

FIG. 4 shows an example of the control of the threshold A given a high variance of the signal height of the electrical signal S. The samples of the electrical signal S that are referenced S1 represent the heart events to be detected such as, for example, the QRS complex, whereas the samples referenced S2 represent disturbing signals such as, for example, the T-waves of the electrocardiogram. Due to the automatic threshold adaptation, the resulting average value MS of the detected signals S leads to the signal heights S2 of the disturbing signals S2 as well as the signal heights S1 of the heart events upwardly exceeding the threshold A, and being detected as heart events. The high variance of the signal parts X1 and X2 exceeding the threshold A, however, indicates misdetection. The variance of the detection margin values X1 and X2 utilized for the formation of the average value is therefore calculated in the formation of the average value. When, as in the example of FIG. 4, the variance exceeds a prescribed value, the threshold A is raised by a given amount ΔA, so that the disturbing signals S2 are no longer erroneously detected as heart events.

Even though circuit blocks of the apparatus of the invention for the detection of heart events are shown in FIG. 2, these circuit blocks are to be interpreted as function blocks. In particular, the described functions can be implemented as a program execution in the detector apparatus 10. Since the formation of the average value, as described, ensues only over a relatively short time interval, or only a few samples of the electrical signal, the calculating outlay required for this purpose is correspondingly small.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for detecting heart events arising in a subject comprising:
   signal pick-up means for acquiring a plurality of successive electrical signals each containing a signal component dependent on a heart event and background signal components, said electrical signal exhibiting a signal height;
   threshold detector means, supplied with said electrical signals from said signal pick-up means, for generating a detector signal indicating a presence of a heart event for each electrical signal having a signal height exceeding a threshold;
   means supplied with said detector signals for identifying a detector margin of each detector signal, said detector margin corresponding to a difference between said signal height and said threshold;
   averaging means, supplied with said respective detector margins for each detector signal, for forming an average value of said detector margins over a time interval corresponding to a few breaths of said subject;
   engageable control means supplied with said average value for adjusting said threshold in relation to said acquired electrical signals by raising said threshold given an increasing average value and lowering said threshold given a decreasing average value, and thereby setting a new threshold; and
   means connected to said control means for generating a switching hysteresis by enabling said control means to set a new threshold only if said average value upwardly transgresses an upper limit value or downwardly transgresses a lower limit value.

2. An apparatus as claimed in claim I wherein said control means is connected to said means for identifying a detector margin for informing said means for identifying a detector margin of said new threshold each time a new threshold is set, and wherein said means for identifying a detector margin thereafter uses said new threshold for identifying said detector margin.

3. An apparatus as claimed in claim 1 wherein said averaging means includes means for setting said time interval to correspond to a predetermined plurality of successive heart events as determined by said threshold detector means.

4. An apparatus as claimed in claim 1 wherein said predetermined plurality is in a range of 10 through 30 successive heart events.

5. A cardiac assist device comprising:
   signal pick-up means for acquiring a plurality of successive electrical signals each containing a signal component dependent on a heart event and background signal components, said electrical signal exhibiting a signal height;
   threshold detector means, supplied with said electrical signals from said signal pick-up means, for generating a detector signal indicating a presence of a heart event for each electrical signal having a signal height exceeding a threshold;
   means supplied with said detector signals for identifying a deflector margin of each detector signal, said detector margin corresponding to a difference between said signal height and said threshold;
   averaging means, supplied with said respective detector margins for each detector signal, for forming an average value of said detector margins over a time interval corresponding to a few breaths of said subject;

enableable control means supplied with said average value for adjusting said threshold in relation to said acquired electrical signals by raising said threshold in relation to said acquired electrical signals by raising said threshold given an increasing value and lowering said threshold given a decreasing average value, and thereby setting a new threshold;

means connected to said control means for generating a switching hysteresis by enabling said control means to set a new threshold only if said average value upwardly transgresses an upper limit value or downwardly transgresses a lower limit value; and a stimulation pulse generator means, supplied with said detector signals, for generating a stimulation pulse if a detector signal is not present within a base time interval following a preceding stimulation pulse or a preceding detector signal, and wherein said control means includes means for lowering said threshold of said threshold detector means by a predetermined amount after a first generation of a stimulation pulse following a detector signal.

6. An apparatus as claimed in claim 1 wherein said control means includes means for identifying a beat-to-beat variance of the signal heights of successive electrical signals used for forming said average value, and for raising said threshold by a predetermined amount if said variance exceeds a predetermined variance value.

7. An apparatus as claimed in claim 6 further comprising means for triggering said means for identifying said beat-to-beat variance only when the threshold of said threshold detector means is set below a minimum threshold value.

8. A method for detecting heart events arising in a subject comprising the steps of:
acquiring a plurality of successive electrical signals from a heart, each containing a signal component dependent on a heart event and background signal components, said electrical signal exhibiting a signal height;
generating a detector signal indicating a presence of a heart event for each electrical signal having a signal height exceeding a threshold; identifying a detector margin of each detector signal, said detector margin corresponding to a difference between said signal height and said threshold;
forming an average value of said detector margins over a time interval corresponding to a few breaths of said subject;
adjusting said threshold in relation to said acquired electrical signals by raising said threshold given an increasing average value and lowering said threshold given a decreasing average value, and thereby setting a new threshold; and
generating a switching hysteresis by setting a new threshold only if said average value upwardly transgresses an upper limit value or downwardly transgresses a lower limit value.

9. A method as claimed in claim 8 wherein the step of identifying a detector margin is further defined by identifying a detector margin using said new threshold each time a new threshold is set.

10. A method as claimed in claim 8 comprising the additional step of setting said time interval, over which said average is formed, to correspond to a predetermined plurality of successive heart events as determined by the steps of generating a detector signal.

11. A method as claimed in claim 10 wherein said predetermined plurality is in a range of 10 through 30 successive heart events.

12. A cardiac assist method comprising the steps of:
acquiring a plurality of successive electrical signals from a heart, each containing a signal component dependent on a heart event and background signal components, said electrical signal exhibiting a signal height;
generating a detector signal indicating a presence of a heart event for each electrical signal having a signal height exceeding a threshold;
identifying a detector margin of each detector signal, said detector margin corresponding to a difference between said signal height and said threshold;
forming an average value of said detector margins over a time interval corresponding to a few breaths of said subject;
adjusting said threshold in relation to said acquired electrical signals by raising said threshold given an increasing average value and lowering said threshold given a decreasing average value, and thereby setting a new threshold;
generating a switching hystersis by setting a new threshold only if said average value upwardly transgresses an upper limit value or downwardly transgresses a lower limit value;
administering a stimulation pulse to said heart if a detector signal is not generated within a base time interval following a preceding stimulation pulse or a preceding detector signal; and
lowering said threshold by a predetermined amount after a first administering of a stimulation pulse following a detector signal.

13. A method as claimed in claim 8 comprising the additional steps of:
identifying a beat-to-beat variance of the signal heights of successive electrical signals used for forming said average value; and
raising said threshold by a predetermined amount if said variance exceeds a predetermined variance value.

14. A method as claimed in claim 13 wherein the step of identifying a beat-to-beat variance is further defined by identifying said beat-to-beat variance only when said threshold is set below a minimum threshold value.

* * * * *